(12) United States Patent
Ogawa et al.

(10) Patent No.: US 7,455,638 B2
(45) Date of Patent: Nov. 25, 2008

(54) ENDOSCOPE APPARATUS WITH A FLUORESCENT MEMBER

(75) Inventors: Kiyotomi Ogawa, Fuchu (JP); Yutaka Konomura, Tachikawa (JP)

(73) Assignee: Olympus Corporation (JP)

( * ) Notice: Subject to any disclaimer, the term of this patent is extended or adjusted under 35 U.S.C. 154(b) by 20 days.

(21) Appl. No.: 11/616,694

(22) Filed: Dec. 27, 2006

(65) Prior Publication Data

US 2007/0149858 A1 Jun. 28, 2007

(51) Int. Cl.
*A61B 1/06* (2006.01)
(52) U.S. Cl. .................. 600/178; 600/180; 600/182; 362/84; 250/484.4
(58) Field of Classification Search ................ 600/178, 600/180, 182, 118, 129; 362/574, 572, 84, 362/260; 250/483.1, 484.4
See application file for complete search history.

(56) References Cited

U.S. PATENT DOCUMENTS

| | | | | |
|---|---|---|---|---|
| 4,448,547 | A * | 5/1984 | Wickersheim | 374/131 |
| 5,037,615 | A * | 8/1991 | Kane | 422/82.08 |
| 5,079,678 | A * | 1/1992 | Parker | 362/84 |
| 5,606,163 | A * | 2/1997 | Huston et al. | 250/337 |
| 6,079,861 | A * | 6/2000 | Woodward et al. | 362/552 |
| 6,114,704 | A * | 9/2000 | Buck | 250/372 |
| 6,814,699 | B2 * | 11/2004 | Ross et al. | 600/179 |
| 2004/0147809 | A1 * | 7/2004 | Kazakevich | 600/178 |
| 2006/0069313 | A1 * | 3/2006 | Couvillon et al. | 600/179 |
| 2006/0116553 | A1 * | 6/2006 | Dunki-Jacobs et al. | 600/179 |
| 2006/0152926 | A1 * | 7/2006 | Hama et al. | 362/231 |
| 2006/0235277 | A1 * | 10/2006 | Ohkubo et al. | 600/179 |

FOREIGN PATENT DOCUMENTS

| | | |
|---|---|---|
| JP | 3194660 | 6/1995 |
| JP | 2005-205195 | 8/2005 |

* cited by examiner

*Primary Examiner*—John P Leubecker
(74) *Attorney, Agent, or Firm*—Ostrolenk, Faber, Gerb & Soffen, LLP

(57) ABSTRACT

The endoscope apparatus of the present invention comprises an insertion section inserted into a space to be inspected, a light emitting device for emitting excitation light, a fluorescent member for emitting illumination light obtained by mixing the excitation light and fluorescent light excited by the excitation light into the space from the tip end of the insertion section, an optical sensor for detecting return light, a part of the illumination light, a light guide for light detection provided with one end facing the fluorescent member and the other end facing the optical sensor for transmitting the return light emitted from the fluorescent member to the optical sensor, a wavelength limiting member provided between the other end of the light guide and the optical sensor for limiting the wavelength of the return light, and a light detection portion for detecting intensity of the return light detected at the optical sensor.

32 Claims, 5 Drawing Sheets

ENDOSCOPE APPARATUS WITH A FLUORESCENT MEMBER

This application claims benefit of Japanese Application No. 2005-380206 filed in Japan on Dec. 28, 2005, the contents of which are incorporated by this reference.

BACKGROUND OF THE INVENTION

1. Field of the Invention

The present invention relates to an endoscope apparatus provided with an insertion section to be inserted into a space to be inspected and a fluorescent member for emitting illumination light obtained by mixing excitation light and fluorescent light into the space to be inspected from a tip end of the insertion section.

2. Description of the Related Art

As well known, the endoscope apparatus is widely used in the medical and industrial fields. The endoscope apparatus used in the medical field is capable of observation of organs in a body cavity and various treatments using a treatment instrument inserted into an insertion channel of the treatment instrument as necessary by inserting an elongated insertion section of the endoscope into the body cavity to be the space to be inspected.

Also, the endoscope apparatus used in the industrial field is capable of observation of scratches, corrosion and the like and various treatments of a porion to be inspected by inserting the elongated insertion section of the endoscope into a jet engine, a piping in a plant and the like to be the space to be inspected.

The endoscope apparatus generally comprises an endoscope containing an image capturing unit disposed at the tip end including an image pickup device such as an image capturing lens, CCD and the like disposed and an elongated insertion section in which an illumination light irradiation unit provided with a light guide and the like for illuminating inside the space to be inspected from the tip end and a device body to which the endoscope is connected.

Also, in the device body, various members for driving the endoscope, specifically, electric parts such as an image processing unit for driving the image capturing unit and processing an image signal of a subject outputted from the image capturing unit, a light source for irradiating the illumination light and the like are disposed.

Here, as the light source of the endoscope apparatus, lamps with relatively large power consumption such as a halogen lamp, xenon lamp, metal halide lamp and the like are generally employed to illuminate the inside of the space to be inspected brightly, but recently, in order to reduce power consumption, endoscope apparatuses employing a semiconductor light-emitting device with low power consumption such as light emitting diode (LED), laser diode (LD) and the like as the light source are well known as disclosed in Japanese Unexamined Patent Application Publication No. 2005-205195, for example.

In the endoscope apparatus disclosed in Japanese Unexamined Patent Application Publication No. 2005-205195, such a configuration is disclosed that an LD is employed for the light source, and excitation light with short wavelength emitted from the LD, blue laser light, for example, is transmitted to a fluorescent member disposed at the tip end of an insertion section through an optical fiber, which is a light guide for illumination disposed at the insertion section of the endoscope, and the blue laser light and the fluorescent light in green and red excited by the laser light are mixed in the fluorescent member so that the illumination light having been converted to white light is used to illuminate inside the space to be inspected.

Also, such a configuration is well known that an optical sensor for detecting intensity of return light, which is a part of the illumination light irradiated from the fluorescent member is provided at the tip end of the insertion section or the device body so that a failure of the LD or bending of the light guide for illumination is detected from the intensity of the return light and power supply to the LD can be controlled based on the detection result.

SUMMARY OF THE INVENTION

The endoscope apparatus of the present invention in brief comprises an insertion section to be inserted into a space to be inspected, a light emitting device for emitting excitation light, a fluorescent member for emitting illumination light obtained by mixing the excitation light and fluorescent light excited by the excitation light into the space to be inspected from the tip end of the insertion section, an optical sensor for detecting return light, which is a part of the illumination light, a light guide for light detection provided with one end facing the fluorescent member and the other end facing the optical sensor for transmitting the return light emitted from the fluorescent member to the optical sensor, a wavelength limiting member provided between above-mentioned the other end of the light guide for light detection and the optical sensor for limiting the wavelength of the return light, and a light detection portion for detecting intensity of the return light detected at the optical sensor.

The above and other objects, features and advantages of the invention will become more clearly understood from the following description referring to the accompanying drawings.

DETAILED DESCRIPTION OF THE PREFERRED EMBODIMENTS

Embodiments of the present invention will be described below referring to the accompanying drawings. An industrial endoscope apparatus is used in the description as an example of the endoscope apparatus.

First Embodiment

Figure 1:
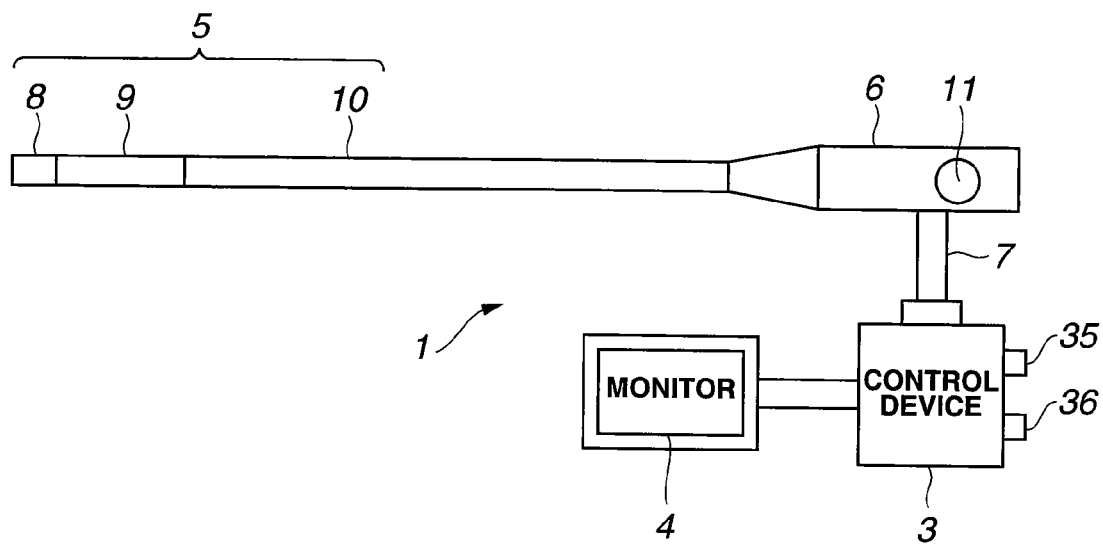
FIG. 1 is a diagram schematically showing an appearance of an endoscope apparatus showing a first embodiment of the present invention.
Figure 2:
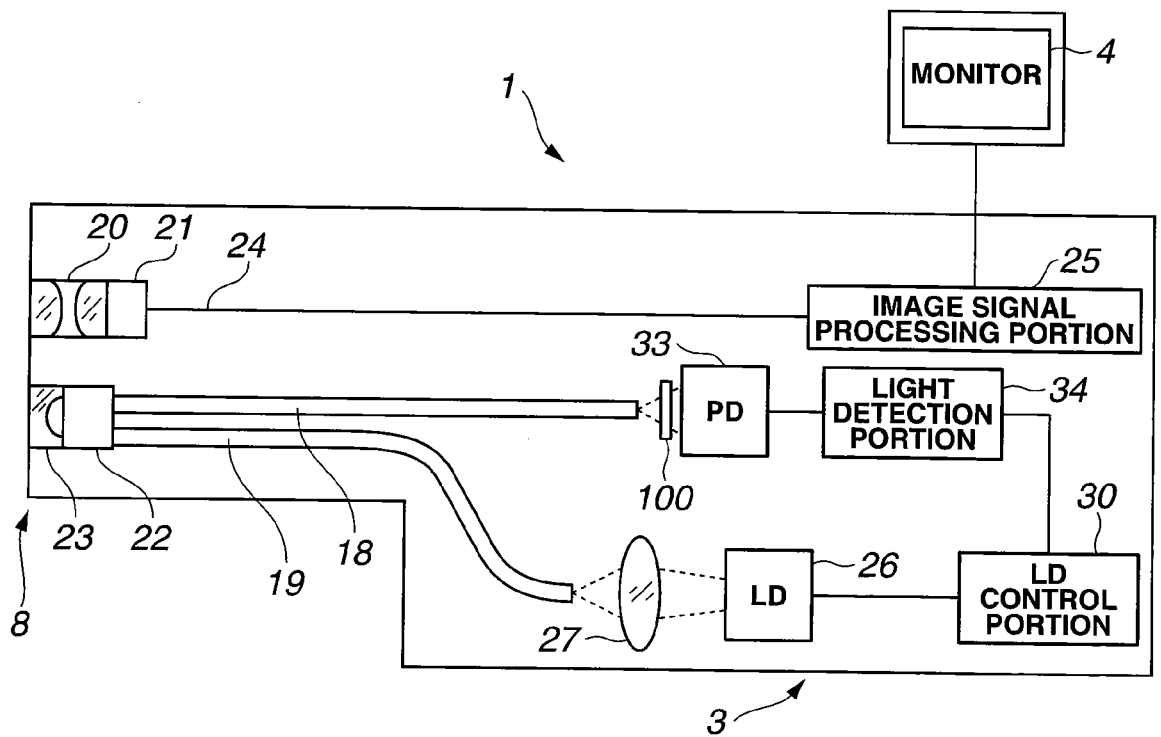
FIG. 2 is a diagram schematically showing an internal configuration of the endoscope apparatus in FIG. 1.

FIG. 1 is a diagram schematically showing an appearance of an endoscope apparatus showing the first embodiment of the present invention, and FIG. 2 is a diagram schematically showing an internal configuration of the endoscope apparatus in FIG. 1.

As shown in these figures, an endoscope apparatus 1 contains major sections comprising a device body 3, a monitor 4 on which an endoscopic image is displayed, an elongated insertion section 5 having flexibility to be inserted into a space to be inspected, an operation portion 6 connected to the base end in the insertion direction of the insertion section 5 and gripped by an operator, and a universal cord 7 extended from the operation portion 6 and having flexibility. In the device body 3, a main switch 35, which is a power switch of the entire endoscope apparatus 1, and a lamp switch 36, which is a switch of a light source provided in the device body 3 are disposed.

At the insertion section 5, a tip end section 8, a bending section 9 formed by consecutively connecting a plurality of bending pieces capable of rotation, and a lengthy flexible tube section 10 formed by a flexible member are consecutively provided in the order from the tip end side of the insertion section 5, and the base end of the flexible tube section 10 is connected to the operation portion 6. The bending section 9 is curved in the vertical/horizontal direction, for example, by bending operation of a bending operation knob 11 of the operation portion 6.

Inside the tip end section 8, as shown in FIG. 2, an objective optical system 20 for forming an observation image inside the space to be inspected, an image pickup device 21 such as a CCD for converting the observation image of the inside of the space to be inspected formed by the objective optical system 20 into an image signal, which is an electric signal, a fluorescent member 22 for emitting illumination light for illuminating the inside of the space to be inspected, and an illumination optical system 23 for controlling light distribution of the illumination light are provided. The illumination light is constituted by mixing the excitation light emitted from an LD 25, which will be described later, and fluorescent light excited by the excitation light.

An image signal line 24 is connected to the image pickup device 21 and transmits an image signal converted by the image pickup device 21 to an image signal processing portion 25 provided in the device body 3. The image signal processing portion 25 coverts the transmitted image signal to a TV signal and outputs it as an endoscopic image to the monitor 4.

Also, as shown in FIG. 2, in the device body 3, other than the image signal processing portion 25, a light emitting device to be a light source for emitting excitation light such as a laser diode (LD) 26, for example, an LD control portion 30, which is a light source control portion for controlling driving of the LD 26, and a light collecting optical system 27 for collecting the excitation light with a short wavelength emitted from the LD 26 such as blue laser light with the wavelength of 445 nm, for example, are provided.

In the insertion section 5 and the universal cord 7, the laser light emitted from the light collecting optical system 27 enters the other end of an optical fiber 19 for illumination, which is a light guide for illumination disposed with one end facing the fluorescent member 22 and the other end facing the focus of the light collecting optical system 27. The illumination optical fiber 19 is comprised by a single optical fiber.

The laser light entering the other end of the illumination optical fiber 19 is passed through the illumination optical fiber 19 and transmitted to one end side of the illumination optical fiber 19 and then, irradiated to the fluorescent member 22.

A fluorescent material contained in the fluorescent member 22 emits fluorescent light of red light and green light with laser light as excitation light. The fluorescent light is mixed with blue light diffused in the fluorescent member 22 to become white light to be the illumination light and is emitted by the illumination optical system 23 into the space to be inspected.

Moreover, as shown in FIG. 2, in the device body 3, a light detection portion 34 connected to the LD control portion 30, a photo diode (PD) 33, which is an optical sensor connected to the light detection portion 34, and an optical filter 100, which is a wavelength limiting member provided on a path of light emitted from the other end of an optical fiber 18 for light detection, which will be described later, between the other end of the light detection optical fiber 18 and the PD 33 are provided.

The optical filter 100 is a filter which limits and transmits the wavelength of return light, which is a part of the illumination light to have the return light after transmission detected by the PD 33, specifically a filter to reflect or absorb the blue light, which is the excitation light, out of the return light, to transmit only fluorescent light and to have the fluorescent light detected by the PD 33.

The PD 33 detects the return light to be entered, specifically the fluorescent light transmitted through the optical filter 100, and the light detection portion 34 detects intensity of the fluorescent light detected at the PD 33 under driving control of the LD control portion 30, which will be described later.

In the insertion section 5 and the universal cord 7, the return light of the illumination light emitted from the fluorescent member 22 is made to enter, one end of the light detection optical fiber 18, which is a light detection light guide disposed with one end facing the fluorescent member 22 and the other end facing the PD 33. The light detection optical fiber 18 is comprised by a single optical fiber.

The return light entered from one end of the light detection optical fiber 18 is passed through the light detection optical fiber 18 and transmitted to the other end side of the light detection optical fiber 18 and then, made to enter the optical filter 100.

Then, at the optical filter 100, after only the fluorescent light out of the return light is transmitted, the fluorescent light is made to enter the PD 33 and detected and then, the intensity of the fluorescent light detected by the PD 33 is detected by the light detection portion 34 under the driving control of the LD control portion 30, which is a control portion, so that deterioration of the fluorescent member 22 is detected by the LD control portion 30 from the detected intensity.

Next, action of the embodiment configured as above will be described. First, when the main switch 35 is turned on, the entire endoscope apparatus 1 is powered on, and an image of a subject inside the space to be inspected formed on the image pickup device 21 is converted to a TV signal at the image signal processing portion 25 and displayed as an endoscopic image on the monitor 4.

In the state where the main switch 35 is turned on, when the lamp switch 36 is turned on, the LD 26 is driven by driving control of the LD control portion 30, and the excitation light emitted from the LD 26, blue laser light, for example, enters the fluorescent member 22 through the illumination optical fiber 19.

After that, the fluorescent light of red light and green light is emitted from the fluorescent member 22 with the blue laser light as excitation light, and the fluorescent light is mixed with the blue light diffused in the fluorescent member 22 and becomes white light to be the illumination light, and the white light is emitted by the illumination optical system 23 into the space to be inspected to illuminate the subject.

At this time, return light of the illumination light passes through the light detection optical fiber 18 and enters the optical filter 100. After that, in the return light, only the fluorescent light is transmitted through the optical filter 100 and the transmitted fluorescent light enters the PD 33. That is, the fluorescent light is detected by the PD 33.

After that, under the driving control of the LD control portion 30, the intensity of the fluorescent light detected at the PD 33 is detected by the light detection portion 34, and deterioration of the fluorescent member 22 is detected by the LD control portion 30 from the detected intensity.

Specifically, at the light detection portion 34, if the intensity of the fluorescent light is not detected or if the intensity of the detected fluorescent light is smaller than a predetermined value, specifically, the intensity of ordinary fluorescent light used for inspection in the space to be inspected and a half or less of the intensity, for example, is detected, it is detected by the LD control portion 30 that the fluorescent light member 22 is deteriorated.

After that, by the LD control portion 30, stop control of emission of the laser light from the LD 26 is carried out. Specifically, driving of the LD 26 is stopped. At this time, the LD 26 may be driving-controlled so that the driving of the LD 26 is not fully stopped but the LD 26 is lighted with such an output that laser light is not emitted from the LD 26.

In this way, in this embodiment, it is shown that the optical filter 100 which reflects or absorbs blue light out of the return light of the irradiated light and transmits only the fluorescent light is provided between the other end of the light detection optical fiber 18 in the device body 3 and the PD 33 on the path of the light emitted from the other end of the light detection optical fiber 18.

Also, in the device body 3, the PD 33 for detecting the fluorescent light transmitted through the optical filter 100 and the light detection portion 34 for detecting the intensity of the fluorescent light are provided, and moreover, the LD control portion 30 is provided for detecting deterioration of the fluorescent member 22 and executing the driving control to stop emission of the laser light from the LD 26 based on the detection of the deterioration.

According to this, even if the fluorescent member 22 is deteriorated, the LD control portion 30 can surely detect deterioration of the fluorescent member 22 through the light detection optical fiber 18, the optical filter 100, the PD 33 and the light detection portion 34.

Thus, the endoscope apparatus 1 can be provided having the configuration that can surely detect drop of intensity of the fluorescent light or non-irradiation of the fluorescent light involved with the deterioration of fluorescent member 22.

A variation is shown below.

In this embodiment, the blue laser light is shown to be used in the example as the excitation light emitted from the LD 26, but not limited to this, it is needless to say that any excitation light with a short wavelength, an ultraviolet ray, for example, may be used as the excitation light.

Also, the semiconductor light-emitting device is not limited to the LD, but it is needless to say that any semiconductor light-emitting device with low power consumption such as a light-emitting diode (LED), for example, may be used.

Also, in this embodiment, the LD control portion 30 is shown to stop emission of the laser light from the LD 26 upon detection of the deterioration of the fluorescent member 22, but in addition to that, the LD control portion 30 may notify deterioration of the fluorescent member 22 to a user by driving control issuing a warning sound, a warning indication or the like after detection of the deterioration of the fluorescent member 22.

Moreover, in this embodiment, the LD control portion 30 is shown to detect the deterioration of the fluorescent member 22, but not limited to this, if the detection of the fluorescent light is not carried out by the PD 33, the LD control portion 30 can also detect breakage of the illumination optical fiber 19.

Also, in this embodiment, the light detection optical fiber 18, which is a light guide, and the illumination optical fiber 19 are shown to be configured by a single optical fiber, but not limited to this, they may be optical fiber bundle bundling a plurality of optical fibers.

Figure 3:
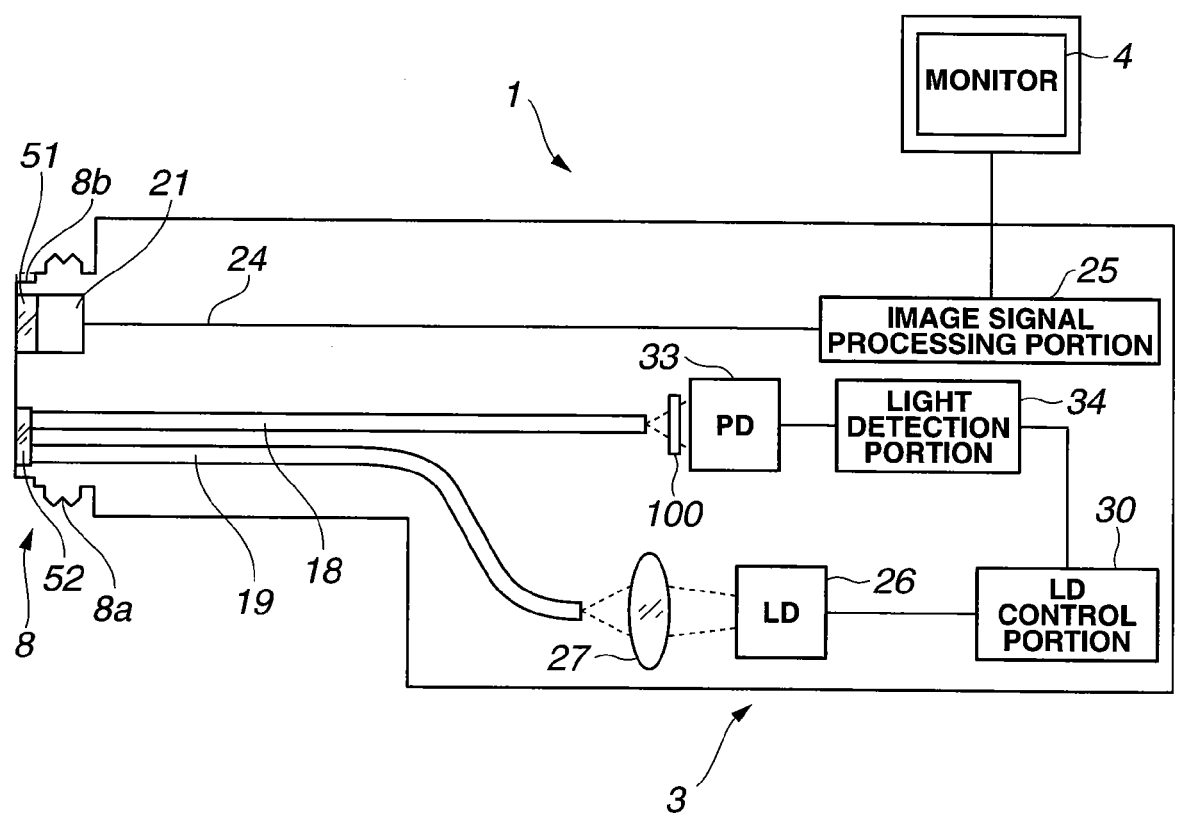
FIG. 3 is a diagram schematically showing a variation of the internal configuration of the endoscope apparatus in FIG. 1 with a section only of a tip end section of an insertion section.

Another variation will be described below using FIGS. 3 to 5. FIG. 3 shows a variation of the internal configuration of the endoscope apparatus in FIG. 1 in a schematic manner with a section of only the tip end section of the insertion section, FIG. 4 is a partial sectional view showing an optical adapter detachably attached at the tip end section of the insertion section of the endoscope apparatus in FIG. 3, and FIG. 5 is a partial sectional view showing a state where the optical adapter in FIG. 4 is attached to the tip end section of the insertion section of the endoscope apparatus in FIG. 3.

As shown in FIG. 3, in the tip end section 8, a male thread 8a is formed on the outer circumference of the tip end section 8, and a positioning groove 8b is formed on the outer circumference of the tip end section 8 closer to the tip end side than the male thread 8a. The male thread 8a is a thread for attaching an optical adapter 40 to the tip end section 8.

Inside the tip end section 8, the image pickup device 21 and the tip end sides of the illumination optical fiber 19 and the light detection optical fiber 18 are arranged, and the image pickup device 21 is protected by an image pickup device cover glass 51 and the tip end sides of the illumination optical fiber 19 and the light detection optical fiber 18 are protected by an optical fiber cover glass 52.

Figure 4:
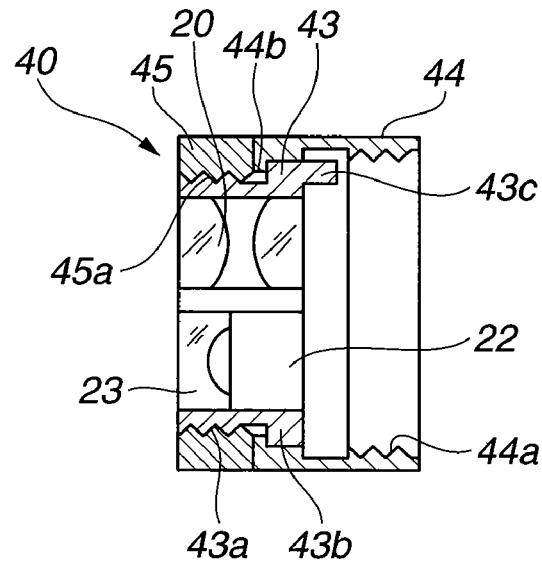
FIG. 4 is a partial sectional view showing an optical adapter which can be detachably attached to the tip end section of the insertion section of the endoscope apparatus in FIG. 3.
Figure 5:
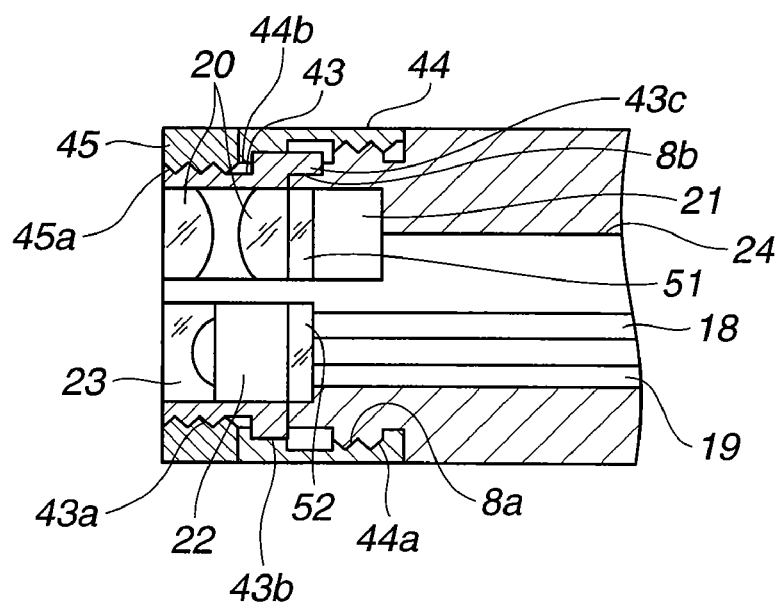
FIG. 5 is a partial sectional view showing a state where the optical adapter in FIG. 4 is attached to the tip end section of the insertion section of the endoscope apparatus in FIG. 3.

As shown in FIG. 4, the optical adapter 40 contains major sections comprised by a substantially cylindrical adapter body 43, a substantially columnar retaining ring 44, and a retainer 45. Inside the adapter body 43, the objective optical system 20 for forming an observation image of the subject on the image pickup device 21, the fluorescent member 22 emitting the fluorescent light with the laser light emitted from the LD 26 as excitation light, and the illumination optical system 23 for emitting the illumination light, which is the white light emitted from the fluorescent member 22, into the space to be inspected are arranged.

On the outer circumference of the tip end side of the adapter body 43, a male thread 43a is formed, and the male thread 43a is screwed with a female thread 45a formed on the inner circumference of the retainer 45. On the outer circumference of the insertion section side of the adapter body 43, a retaining ring engagement section 43b is formed to be engaged with the retaining ring 44.

By engaging the retaining ring engagement section 43b with an adapter engagement section 44b formed on the inner circumference on the tip end side of the retaining ring 44, the retaining ring 44 is constituted rotatable with respect to the adapter body 43.

Also, by adhesive fixation of the screwed section between the female thread 45a of the retainer 45 and the male thread 43a of the adapter body 43, the retaining ring 44 is configured so as not to be removed from the adapter body 43.

On the inner circumference of the insertion section 5 side of the retaining ring 44, a female thread 44a is formed, and by screwing the female thread 44a with the male thread 8a on the outer circumference of the tip end section 8, the optical adapter 40 is attached to the tip end section 8.

On the surface of the insertion section 5 side of the adapter body 43, a positioning projection 43c is formed. The positioning projection 43c is fitted with the positioning groove 8b at the tip end section 8 when the optical adapter 40 is attached to the tip end section 8, and rotation of the adapter body 43 with respect to the tip end section 8 is restricted.

By this, when the optical adapter 40 is attached to the tip end section 8, the objective optical system 20 is arranged at a position opposite to the image pickup device 21, and the illumination optical system 23 and the fluorescent member 22 are arranged at positions opposite to the tip end sides of the illumination optical fiber 19 and the light detection optical fiber 18.

As shown in FIG. 5, in the state where the optical adapter 40 is attached to the tip end section 8, the female thread 44a on the inner circumference of the retaining ring 44 and the male thread 8a on the outer circumference of the tip end section 8 are screwed together, and the positioning projection 43c of the adapter body 43 is fitted in the positioning groove 8b of the tip end section 8.

In this way, by constituting the optical adapter 40 detachable with respect to the tip end section 8, the characteristic of the objective optical system 20 can be changed by replacing the optical adapter 40, and the optimal view angle, observation direction and focal depth can be selected according to a subject. The other configurations are the same as those of the above-mentioned first embodiment.

In the state where the optical adapter 40 is attached, the laser light, which is the excitation light emitted from the LD 26, travels through the light collecting optical system 27, the illumination optical fiber 19, the optical fiber cover glass 52 and is irradiated to the fluorescent member 22.

The return light of the white light, which is the illumination light emitted from the fluorescent member 22, goes through the light detection optical fiber 18, and only the fluorescent light is extracted when transmitted through the optical filter 100. And then, it is detected by the PD 33 and the intensity of the fluorescent light is, as mentioned above, detected by the light detection portion 34 under the driving control of the LD control portion 30.

In this way, if the fluorescent member 22 is configured to be disposed at the optical adapter 40, when the optical adapter 40 is removed from the tip end section 8, the laser light is not irradiated to the fluorescent member 22 from the LD 26 any more and the white light, which is the illumination light, is not emitted, and the fluorescent light is not detected at the PD 33 any more.

Thus, as mentioned above, since the driving control to stop emission of the laser light from the LD 26 is carried out by the LD control portion 30, a user can attach/remove the optical adapter 40 to/from the tip end section 8 without sensing glare, which improves workability. At this time, as with the above mentioned embodiment, the same effect can be obtained by driving control of the LD 26 so that the driving of the LD 26 is not fully stopped but lighted at such an output that the laser light is not emitted from the LD 26.

Also, since the fluorescent member 22 can be replaced by a fluorescent member with another characteristic by replacing the optical adapter 40, the wavelength of the light illuminating inside the space to be inspected can be easily changed. From this, the user can select the illumination with the wavelength suitable for the subject. The other effects are the same as those in the above-mentioned first embodiment.

Attachment/detachment of the optical fiber 40 with respect to the tip end section 8 is not limited to the above-mentioned screwing of the threads, but lock structure and the like by fixing by a screw or engagement between projections and recesses may be used.

Second Embodiment

Figure 6:
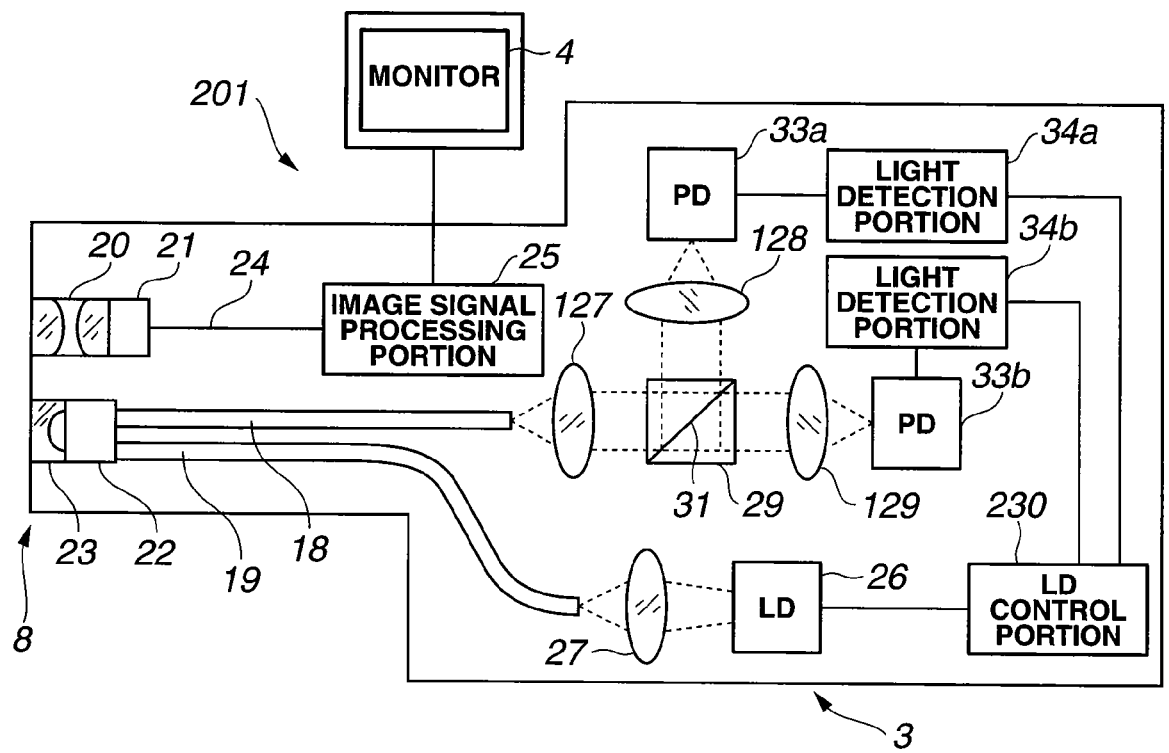
FIG. 6 is a diagram schematically showing the internal configuration of the endoscope apparatus showing a second embodiment of the present invention.

FIG. 6 is a diagram schematically showing the internal configuration of the endoscope apparatus of a second embodiment of the present invention.

The configuration and action of an endoscope apparatus 201 of this second embodiment are different from the endoscope apparatus 1 shown in FIGS. 1, 2 in the point that the return light of the illumination light is detected by two PDs. Thus, only the difference will be described and the same configurations as those in the first embodiment are given the same reference numerals and the description will be omitted.

As shown in FIG. 6, in the device body 3, light detection portions 34a, 34b connected to an LD control portion 230, which is a light source control portion, a photo diode (PD) 33a connected to the light detection portion 34a, a photo diode (PD) 33b connected to the light detection portion 34b, and a light splitter 29, which is a wavelength limiting member provided between the other end of the light detection optical fiber 18 and the PD 33a, 33b are provided.

Also, on the input end side of the light splitter 29, specifically, at a position facing the other end of the light detection optical fiber 18, a light collecting optical system 127 is arranged, while on the output end side on one side of the light splitter 29, a light collecting optical system 128 is arranged and a light collecting optical system 129 is arranged on the other output end side. Also, in the vicinity of the focus of the light collecting optical system 128, the PD 33a is arranged, while in the vicinity of the focus of the light collecting optical system 129, the PD 33b is arranged.

The light collecting optical system 127 collects return light of the illumination light emitted from the light detection optical fiber 18 and has it enter the optical splitter 29, the light collecting optical system 128 collects fluorescent light, which will be described later, emitted from the light splitter 29 and has it enter the PD 33a, and the light collecting optical system 129 collects excitation light, which will be described later, emitted from the light splitter 29 and has it enter the PD 33b.

The light splitter 29 is comprised by two right angle prisms, and formed in a cube shape by bonding inclined faces of the two right angle prisms. Also, the light splitter 29 has a reflective film 31 with wavelength selectivity deposited on the inclined face of one of the prisms.

The reflective film 31 is comprised by either of a thin film which transmits the excitation light and reflects the fluorescent light in the return light of the illumination light or a thin film which reflects the excitation light and transmits the fluorescent light. The reflective film 31 will be described below as a thin film which transmits the excitation light and reflects the fluorescent light. In this case, the PD 33a is a first optical sensor for detecting only the fluorescent light, while the PD 33b constitutes a second optical sensor for detecting only the excitation light.

The light splitter 29 containing the above configuration is a splitter which limits the wavelength of the return light of the illumination light and executes at least one of transmission or reflection and has the excitation light and the fluorescent light after transmission or reflection detected by the respective PDs.

Specifically, the light splitter 29 is a splitter which transmits the blue light, which is the excitation light toward the PD 33b to have the PD 33b detect the blue light and reflects the fluorescent light toward the PD 33a to have the PD 33a detect the fluorescent light.

The light detection portion 34a detects the intensity of the fluorescent light detected at the PD 33a under the driving control of the LD control portion 230, and the light detection portion 34b detects the intensity of the excitation light detected at the PD 33b under the driving control of the LD control portion 230.

The LD control portion 230 detects deterioration of the fluorescent member 22 by detecting the intensity of the fluorescent light detected at the PD 33a by driving control of the light detection portion 34a and by detecting the intensity of the excitation light detected at the PD 33b by driving control of the light detection portion 34b so as to detect the intensity of the fluorescent light compared to the intensity of the excitation light.

Specifically, if the intensity of the fluorescent light is not detected at the light detection portion 34a, or if the intensity of the fluorescent light compared to the intensity of the detected excitation light is smaller than a predetermined value, specifically, the intensity of the fluorescent light used for inspection in the space to be inspected, a half or less of a usual intensity is detected, for example, it is detected by the LD control portion 230 that the fluorescent member 22 is deteriorated.

After that, control to stop emission of the laser light from the LD 26 is executed by the LD control portion 230. Specifically, the driving of the LD 26 is stopped. At this time, the LD 26 may be drive-controlled so that it is lighted with an output that the laser light is not emitted from the LD 26 without fully stopping the driving of the LD 26.

Next, action of this embodiment configured as above will be described in brief. Since the process till the return light of the illumination light from emission of the laser light by the LD 26 is emitted from the other end of the light detection optical fiber 18 is the same as that of the above-mentioned first embodiment, the description will be omitted.

The return light emitted from the other end of the light detection optical fiber 18 is collected by the light collecting optical system 127 and made to enter the light splitter 29. Then, at the light splitter 29, the blue light, which is the excitation light, is transmitted toward the PD 33b, the transmitted blue light is collected by the light collecting optical system 129, emitted toward the PD 33b and detected by the PD 33b. Also, the fluorescent light is reflected toward the PD 33a, the reflected fluorescent light is collected by the light collecting optical system 128, emitted toward the PD 33a and detected by the PD 33a.

Then, under the driving control of the LD control portion 230, the intensity of the fluorescent light is detected by the light detection portion 34a, and the intensity of the blue light is detected by the light detection portion 34b. After that, since the intensity of the fluorescent light compared to the intensity of the blue light is detected by the LD control portion 230, deterioration of the fluorescent member 22 is detected. Lastly, if the deterioration of the fluorescent member 22 is detected, either control to stop the emission of the laser light from the LD 26 or control to drive the LD 26 so that it is lighted at an output not emitting the laser light from the LD 26 is carried out by the LD control portion 230.

In this way, in this embodiment, it is shown that the fluorescent light and the excitation light are separated from the return light by the light splitter 29 to have the separate PD 33a, 33b detect the fluorescent light and the excitation light, respectively, and the LD control portion 230 measures the intensities of the fluorescent light and the excitation light, respectively, by driving control of the separate light detection portions 34a, 34b and detects the intensity of the fluorescent light compared to the intensity of the excitation light so that the deterioration of the fluorescent member 22 is detected.

According to this, by detecting the deterioration of the intensity of the fluorescent light using two parameters of the intensity of the fluorescent light and the intensity of the excitation light, the deterioration of the fluorescent member 22 can be detected with higher accuracy than that of the first embodiment.

Thus, the endoscope apparatus 201 having a configuration which can surely detect drop of the intensity of the fluorescent light or non-irradiation of the fluorescent light with the deterioration of the fluorescent member 22 can be provided.

Also, the LD control portion 230 can detect breakage of the illumination optical fiber 19 or the LD 26 by detecting only the intensity of the excitation light detected by the PD 33b through driving control of the light detection portion 34b. At this time, the LD control portion 230 executes driving control to fully stop the LD 26 after the breakage of the illumination optical fiber 19 or the LD 26 is detected.

With regard to distinction between the deterioration of the fluorescent member 22 and the breakage of the illumination optical fiber 19 or the LD 26, as mentioned above, if the driving of the LD 26 is not fully stopped but LD 26 is drive-controlled so as to be lighted with an output not emitting the laser light from the LD 26 after detection of the deterioration of the fluorescent member 22, when the LD 26 is being driven even though the laser light is not emitted, the user can determine it as the deterioration of the fluorescent member 22, while if the driving of the LD 26 is completely stopped, the user can determine it as the breakage of the illumination optical fiber 19 or the LD 26.

From this, in this embodiment, the LD control portion 230 can detect the deterioration of the fluorescent member 22 and the breakage of the illumination optical fiber 19 or the LD 26 separately.

A variation will be shown below.

In this embodiment, the reflective film 31 is described as a thin film which transmits the excitation light and reflects the fluorescent light, but it is needless to say that the reflective film 31 may be a thin film which reflects the excitation light and transmits the fluorescent light.

In this case, the light collecting optical system 128 collects the excitation light emitted from the light splitter 29 to have it enter the PD 33a, and the light collecting optical system 129 collects the fluorescent light emitted from the light splitter 29 to have it enter the PD 33b. Also, the PD 33a is the second optical sensor for detecting only the excitation light, while the PD 33b constitutes the first optical sensor for detecting only the fluorescent light.

Thus, the light splitter 29 is a splitter which transmits the fluorescent light toward the PD 33b to have the PD 33b detect the fluorescent light and reflects the excitation light toward the PD 33a to have the PD 33a detect the excitation light.

Also, the light detection portion 34a detects the intensity of the excitation light detected at the PD 33a under the control of the LD control portion 230, and the light detection portion 34b detects the intensity of the fluorescent light detected at the PD 33b under the driving control of the LD control portion 230.

In this embodiment, too, it is needless to say that the excitation light with a short wavelength is not limited to the blue laser light, but an ultraviolet ray, for example, may be used, and the semiconductor light emitting device is not limited to the LD but any semiconductor light emitting device with low power consumption such as a light emitting diode (LED) or the like may be used.

Moreover, the LD control portion 230 may notify the user of the deterioration of the fluorescent member 22 by driving control of emitting a warning sound or a warning indication or the like after detection of the deterioration of the fluorescent member 22.

Furthermore, in the endoscope apparatus 201 of this embodiment, too, as shown in the above-mentioned FIGS. 3 to 5, the optical adapter 40 may be in the configuration detachable to the tip end section 8 of the insertion section 5. The effects in this case are the same as those in the above-mentioned first embodiment.

Third Embodiment

Figure 7:
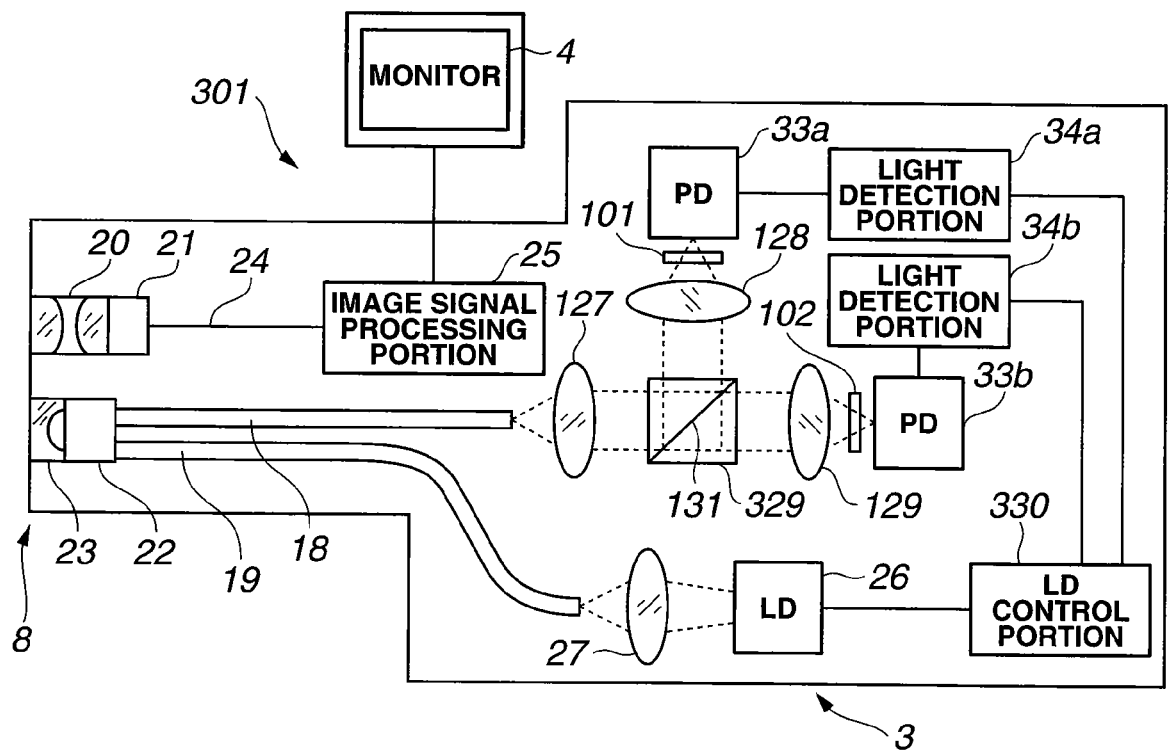
FIG. 7 is a diagram schematically showing the internal configuration of the endoscope apparatus showing a third embodiment of the present invention.

FIG. 7 is a diagram schematically showing the internal configuration of the endoscope apparatus according to a third embodiment of the present invention.

The configuration of an endoscope apparatus 301 of this third embodiment is different from the endoscope apparatus 201 shown in FIG. 6 in the point that the light splitter is configured by a simple half mirror for splitting the entered return light into two directions without limiting the wavelength. Thus, only this difference will be described, and the same configurations as those of the first and the second embodiments are given the same reference numerals, and their description will be omitted.

As shown in FIG. 7, in the device body 3, there are provided the light detection portions 34a, 34b connected to an LD control portion 330, which is a light source control portion, the PD 33a connected to the light detection portion 34a, the PD 33b connected to the light detection portion 34b, a first optical filter 101, which is a wavelength limiting member, a second optical filter 102, which is a wavelength limiting member, and a light splitter 329.

Also, on the input end side of the light splitter 329, specifically, at a position facing the other end of the light detection optical fiber 18, the light collecting optical system 127 is arranged, while on the output end side on one side of the light splitter 329, the light collecting optical system 128 is arranged and the light collecting optical system 129 is arranged on the other output end side.

Also, in the vicinity of the focus of the light collecting optical system 128, the first optical filter 101 is arranged between the light collecting optical system 128 and the PD 33a, while in the vicinity of the focus of the light collecting optical system 129 between the light collecting optical system 129 and the PD 33b, the second optical filter 102 is arranged.

The light collecting optical system 127 collects the return light of the illumination light emitted from the other end of the light detection optical fiber 18 and emits it to the optical splitter 329, the light collecting optical system 128 collects the return light emitted from the light splitter 329 and emits it to the first optical filter 101, and the light collecting optical system 129 collects the return light emitted from the light splitter 329 and emits it to the second optical filter 102.

The light splitter 329 is comprised by two right angle prisms, and formed in a cube shape by bonding inclined faces of the two right angle prisms. Also, the light splitter 329 has a reflective film 131 deposited on an inclined face of one of the prisms, functioning simply as a half mirror to split the return light of the emitted illumination light toward the PD 33a and the PD 33b, respectively.

The PD 33a is the first optical sensor for detecting only the fluorescent light and the PD 33b constitutes the second optical sensor for detecting only the excitation light.

Also, the first optical filter 101 is a filter which limits the wavelength of the return light of the illumination light split by the light splitter 329 and transmits it and has the return light after transmission detected by the PD 33a, specifically a filter which transmits only the fluorescent light and has the fluorescent light after transmission detected by the PD 33a.

The second optical filter 102 is a filter which limits the wavelength of the return light of the illumination light split by the light splitter 329 and transmits it and has the return light after transmission detected by the PD 33b, specifically a filter which transmits only the blue light, which is the excitation light, and has the blue light after transmission detected by the PD 33b.

The light detection portion 34a detects the intensity of the fluorescent light detected at the PD 33a under the driving control of the LD control portion 330, while the light detection portion 34b detects the intensity of the excitation light detected at the PD 33b under the driving control of the LD control portion 330.

The LD control portion 330 detects the intensity of the fluorescent light detected at the PD 33a using the light detection portion 34a and the intensity of the excitation light detected at the PD 33b using the light detection portion 34b and detects the intensity of the fluorescent light compared to the intensity of the excitation light so as to detect the deterioration of the fluorescent member 22.

Specifically, if the intensity of the fluorescent light is not detected at the light detection portion 34a, or if the intensity of the fluorescent light compared to the intensity of the detected excitation light is smaller than a predetermined value, specifically, the intensity of the fluorescent light used for inspection in the space to be inspected, a half or less of a usual intensity is detected, for example, it is detected by the LD control portion 330 that the fluorescent member 22 is deteriorated.

After that, driving control to stop emission of the laser light from the LD 26 is executed by the LD control portion 330. Specifically, the driving of the LD 26 is stopped. At this time, the LD 26 may be drive-controlled so that it is lighted with an output that the laser light is not emitted from the LD 26 without fully stopping the driving of the LD 26.

Next, action of this embodiment configured as above will be described in brief. In this embodiment, too, since the process till the return light of the illumination light from emission of the laser light by the LD 26 is emitted from the other end of the light detection optical fiber 18 is the same as that of the above-mentioned first embodiment, the description will be omitted.

The return light emitted from the other end of the light detection optical fiber 18 is collected by the light collecting optical system 127 and made to enter the light splitter 329. After that, at the light splitter 329, the return light is split toward the PD 33a, 33b, one of the return light is collected by the light collecting optical system 128 and emitted toward the PD 33*a*, and after only the fluorescent light is transmitted through the first optical filter 101, only the fluorescent light is detected by the PD 33*a*.

Also, the other return light is collected by the light collecting optical system 129 and emitted toward the PD 33*b* and only the excitation light is transmitted through the second optical filter 102, and then, only the excitation light is detected by the PD 33*b*.

Next, the intensity of the fluorescent light is detected by the light detection portion 34*a* under the driving control of the LD control portion 330 and the intensity of the excitation light is detected by the light detection portion 34*b*. After that, the intensity of the fluorescent light compared to the intensity of the excitation light is detected by the LD control portion 330, and the deterioration of the fluorescent member 22 is detected. Lastly, when the deterioration of the fluorescent member 22 is detected, control to stop emission of the laser light from the LD 26 or control to drive the LD 26 so that it is lighted with an output not emitting the laser light from the LD 26 is carried out by the LD control portion 330.

In this way, by configuring the endoscope apparatus 301, the same effect as that of the above-mentioned second embodiment can be also obtained. In this embodiment, too, by detecting only the intensity of the excitation light detected at the PD 33*b* using the light detection portion 34*b*, the LD control portion 330 can detect breakage of the illumination optical fiber 19 or the LD 26. At this time, the LD control portion 330 executes the driving control to fully stop the LD 26 after detection of the breakage of the illumination optical fiber 19 or the LD 26.

With regard to distinction between the deterioration of the fluorescent member 22 and the breakage of the illumination optical fiber 19 or the LD 26, as mentioned above, if the driving of the LD 26 is not fully stopped but LD 26 is driven and controlled so as to be lighted with an output not emitting the laser light from the LD 26 after detection of the deterioration of the fluorescent member 22, when the LD 26 is being driven even though the laser light is not emitted, the user can determine it as the deterioration of the fluorescent member 22, while if the driving of the LD 26 is completely stopped, the user can determine it as the breakage of the illumination optical fiber 19 or the LD 26.

From this, in this embodiment, too, the LD control portion 330 can detect the deterioration of the fluorescent member 22 and the breakage of the illumination optical fiber 19 or the LD 26 separately.

A variation will be shown below.

In this embodiment, too, it is needless to say that the excitation light with a short wavelength is not limited to the blue laser light, but an ultraviolet ray, for example, may be used, and the semiconductor light emitting device is not limited to the LD but any semiconductor light emitting device with low power consumption such as a light emitting diode (LED) or the like may be used.

Moreover, the LD control portion 330 may notify the user of the deterioration of the fluorescent member 22 by driving control of emitting a warning sound or a warning indication or the like after detection of the deterioration of the fluorescent member 22.

Furthermore, in the endoscope apparatus 301 of this embodiment, too, as shown in the above-mentioned FIGS. 3 to 5, the optical adapter 40 may be in the configuration detachable to the tip end section 8 of the insertion section 5. The effects in this case are the same as those in the above-mentioned first embodiment.

Fourth Embodiment

Figure 8:
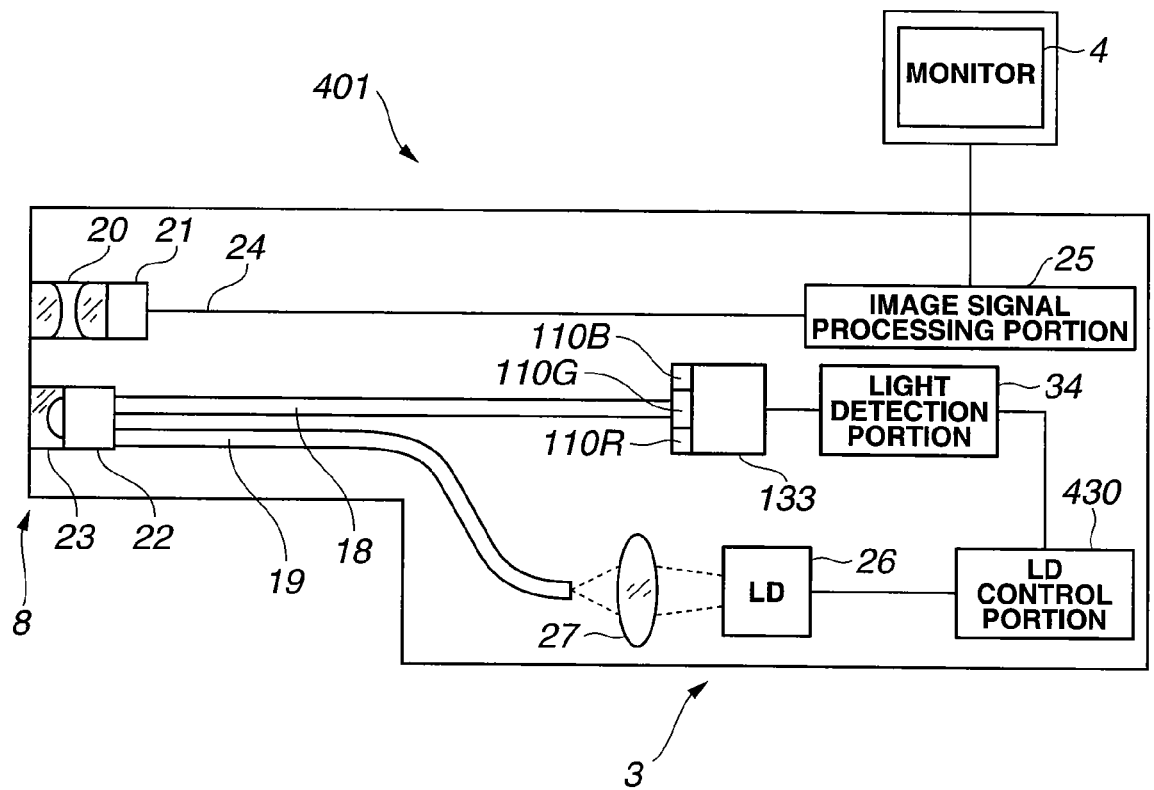
FIG. 8 is a diagram schematically showing the internal configuration of the endoscope apparatus showing a fourth embodiment of the present invention.

FIG. 8 is a view schematically showing the internal configuration of the endoscope apparatus of a fourth embodiment of the present invention.

The configuration of the endoscope apparatus 401 of this fourth embodiment is different from the endoscope apparatus 1 shown in FIGS. 1, 2 in the point that an RGB color sensor in which a three-channel PD which combines color filters having sensitivity in blue, green, red, respectively, is made into a single package transmits the return light of the illumination light after separating it into green, red fluorescent light and blue excitation light. Thus, only the difference will be described and the same configurations as those in the first embodiment are given the same reference numbers and the description will be omitted.

As shown in FIG. 8, in the device body 3, the light detection portion 34 connected to an LD control portion 430, which is a light source control portion, and an RGB color sensor 133, which is an optical sensor connected to the light detection portion 34, are provided.

The RGB color sensor 133 is a color sensor which includes a three-channel PD combining color filters 110R, 110G, 110B having sensitivity in blue, green, red with respect to the return light of the illumination light, respectively, in a single package.

The red color filter 110R and the green color filter 110G are filters which limit the wavelength of the return light of the illumination light and transmit it and have the return light after transmission detected by the RGB color sensor 133, specifically, a first wavelength limiting member which reflects or absorbs the blue excitation light of the return light, transmits only the red, green fluorescent light and has the fluorescent light detected by the RGB sensor 133.

The blue color filter 110B is a filter which limits and transmits the wavelength of the return light of the illumination light and has the return light after transmission detected by the RGB color sensor 133, specifically a second wavelength limiting member which reflects or absorbs the red and green fluorescent light of the return light, transmits only the blue excitation light and has the blue excitation light detected by the RGB color sensor 133.

The light detection portion 34 detects the intensity of the fluorescent light and the intensity of the excitation light detected at the RGB color sensor 133 under the driving control of the LD control portion 430.

The LD control portion 430 detects the intensities of the fluorescent light and the excitation light detected at the color filter 133 using the light detection portion 34 and detects the deterioration of the fluorescent member 22 by detecting the intensity of the fluorescent light compared to the intensity of the excitation light.

Specifically, if the intensity of the fluorescent light is not detected at the RGB color sensor 133, or if the intensity of the fluorescent light compared to the intensity of the detected excitation light is smaller than a predetermined value, specifically, the intensity of the fluorescent light used for inspection in the space to be inspected, a half or less of a usual intensity is detected, for example, it is detected by the LD control portion 430 that the fluorescent member 22 is deteriorated.

After that, driving control to stop emission of the laser light from the LD 26 is executed by the LD control portion 430. Specifically, the driving of the LD 26 is stopped. At this time, the LD 26 may be drive-controlled so that it is lighted with an output that the laser light is not emitted from the LD 26 without fully stopping the driving of the LD 26.

Next, action of this embodiment configured as above will be described in brief. In this embodiment, too, since the process till the return light of the illumination light from emission of the laser light by the LD 26 is emitted from the other end of the light detection optical fiber 18 is the same as that of the above-mentioned first embodiment, the description will be omitted.

The return light emitted from the other end of the light detection optical fiber 18 is emitted to the RGB color filter 133, and only the red, green fluorescent lights out of the return light are transmitted through the red color filter 110R, the green color filter 110G at the RGB color filter 133 and the fluorescent light is detected by the RGB color sensor 133. Also, only the blue excitation light out of the return light is transmitted through the blue color filter 110B and the excitation light is detected by the RGB color sensor 133.

Next, the intensity of the fluorescent light and the intensity of the excitation light are detected by the light detection portion 34 under the driving control of the LD control portion 430. After that, the intensity of the fluorescent light compared to the intensity of the excitation light is detected by the LD control portion 430, and the deterioration of the fluorescent member 22 is detected. Lastly, when the deterioration of the fluorescent member 22 is detected, control to stop emission of the laser light from the LD 26 or control to drive the LD 26 so that it is lighted with an output not emitting the laser light from the LD 26 is carried out by the LD control portion 430.

In this way, by configuring the endoscope apparatus 401, the same effect as that of the above-mentioned first to the third embodiments can be obtained. In this embodiment, too, by detecting only the intensity of the blue excitation light detected at the color filter 133 using the light detection portion 34, the LD control portion 430 can detect breakage of the illumination optical fiber 19 or the LD 26. At this time, the LD control portion 430 executes the driving control to fully stop the LD 26 after detection of the breakage of the illumination optical fiber 19 or the LD 26.

With regard to distinction between the deterioration of the fluorescent member 22 and the breakage of the illumination optical fiber 19 or the LD 26, as mentioned above, if the driving of the LD 26 is not fully stopped but LD 26 is drive-controlled with an output not emitting the laser light from the LD 26 after detection of the deterioration of the fluorescent member 22, when the LD 26 is being driven even though the laser light is not emitted, the user can determine it as the deterioration of the fluorescent member 22, while if the driving of the LD 26 is completely stopped, the user can determine it as the breakage of the illumination optical fiber 19 or the LD 26.

From this, in this embodiment, too, the LD control portion 430 can detect the deterioration of the fluorescent member 22 and the breakage of the illumination optical fiber 19 or the LD 26 separately.

A variation will be shown below.

In this embodiment, too, the LD control portion 430 may notify the user of the deterioration of the fluorescent member 22 by control of emitting a warning sound or a warning indication or the like after detection of the deterioration of the fluorescent member 22.

Furthermore, in the endoscope apparatus 401 of this embodiment, too, as shown in the above-mentioned FIGS. 3 to 5, the optical adapter 40 may be in the configuration detachable to the tip end section 8 of the insertion section 5. The effects in this case are the same as those in the above-mentioned first embodiment.

Also, in the above-mentioned first to the fourth embodiments, the endoscope apparatus is shown in an example of an industrial endoscope apparatus, but it is needless to say that it is not limited to the industrial endoscope apparatuses but can be applied to medical endoscope apparatuses.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An endoscope apparatus comprising:
   an insertion section to be inserted into a space to be inspected;
   a light emitting device for emitting excitation light;
   a fluorescent member for emitting illumination light obtained by mixing the excitation light and fluorescent light excited by the excitation light into the space to be inspected from the tip end of the insertion section;
   an optical sensor for detecting return light, which is a part of the illumination light;
   a light guide for light detection provided with one end facing the fluorescent member and the other end facing the optical sensor for transmitting the return light emitted from the fluorescent member to the optical sensor;
   a wavelength limiting member provided between the other end of the light guide for light detection and the optical sensor for limiting the wavelength of the return light; and
   a light detection portion for detecting intensity of the return light detected at the optical sensor,
   wherein the wavelength limiting member comprises a first wavelength limiting member for transmitting only the fluorescent light out of the return light toward the optical sensor and a second wavelength limiting member for transmitting only the excitation light out of the return light toward the optical sensor.

2. The endoscope apparatus according to claim 1,
   wherein the optical sensor comprises a first optical sensor for detecting the fluorescent light and a second optical sensor for detecting the excitation light.

3. The endoscope apparatus according to claim 2,
   wherein the light detection portion comprises a first light detection portion for detecting intensity of the fluorescent light detected at the first optical sensor and a second light detection portion for detecting intensity of the excitation light detected at the second optical sensor.

4. The endoscope apparatus according to claim 3,
   wherein the wavelength limiting member comprises a light splitter which transmits the excitation light out of the return light toward the second optical sensor and reflects the fluorescent light toward the first optical sensor or reflects the excitation light toward the second optical sensor and transmits the fluorescent light toward the first optical sensor.

5. The endoscope apparatus according to claim 4, further comprising
   a control portion for controlling detection of deterioration of the fluorescent member from the intensity of the return light detected by the light detection portion, and
   wherein the control portion detects the intensity of the fluorescent light detected at the first optical sensor and detects the intensity of the excitation light detected at the second optical sensor; and the control portion carries out control to detect deterioration of the fluorescent member by detecting the intensity of the fluorescent light compared to the intensity of the excitation light.

6. The endoscope apparatus according to claim 5, wherein the control portion carries out control to stop emission of the excitation light from the light emitting device after detection of the deterioration of the fluorescent member.

7. The endoscope apparatus according to claim 3, further comprising
a half mirror which splits the return light toward the first optical sensor and the second optical sensor, and
wherein the wavelength limiting member comprises a first optical filter provided between the first optical sensor and the half mirror for transmitting only the fluorescent light out of the return light toward the first optical sensor and a second optical filter provided between the second optical sensor and the half mirror for transmitting only the excitation light out of the return light toward the second optical sensor.

8. The endoscope apparatus according to claim 7, further comprising
a control portion for controlling detection of deterioration of the fluorescent member from the intensity of the return light detected by the light detection portion, and
wherein the control portion detects the intensity of the fluorescent light detected at the first optical sensor and detects the intensity of the excitation light detected at the second optical sensor; and
the control portion carries out control to detect deterioration of the fluorescent member by detecting the intensity of the fluorescent light compared to the intensity of the excitation light.

9. The endoscope apparatus according to claim 8, wherein the control portion carries out control to stop emission of the excitation light from the light emitting device after detection of the deterioration of the fluorescent member.

10. The endoscope apparatus according to claim 3, further comprising
a control portion for controlling output of the light emitting device based on a detection result of the first light detection portion and the second light detection portion.

11. The endoscope apparatus according to claim 2, further comprising
a control portion for controlling detection of deterioration of the fluorescent member from the intensity of the return light detected by the light detection portion, and
wherein the wavelength limiting member transmits only the fluorescent light out of the return light and has only the fluorescent light detected by the optical sensor; and
the control portion detects the intensity of the fluorescent light detected at the optical sensor and carries out control to detect deterioration of the fluorescent member.

12. The endoscope apparatus according to claim 1, further comprising
a control portion for controlling output of the light emitting device based on a detection result of the light detection portion.

13. The endoscope apparatus according to claim 1, wherein the wavelength limiting member is an optical filter for transmitting only the fluorescent light out of the return light.

14. The endoscope apparatus according to claim 1, further comprising
a light guide for illumination provided having one end facing the fluorescent member and the other end facing the light emitting device for transmitting the excitation light emitted from the light emitting device to the fluorescent member.

15. The endoscope apparatus according to claim 1, further comprising
an optical adapter detachably mounted at the tip end of the insertion section, and
wherein the fluorescent member is provided at the optical adapter.

16. The endoscope apparatus according to claim 1, further comprising
a control portion for controlling detection of deterioration of the fluorescent member from the intensity of the return light detected by the light detection portion.

17. The endoscope apparatus according to claim 16, wherein the control portion carries out control to stop emission of the excitation light from the light emitting device after detection of the deterioration of the fluorescent member.

18. The endoscope apparatus according to claim 1, further comprising
a control portion for controlling detection of deterioration of the fluorescent member from the intensity of the return light detected by the light detection portion, and
wherein the control portion detects the intensity of the fluorescent light detected at the first optical sensor and detects the intensity of the excitation light detected at the second optical sensor; and
the control portion carries out control to detect deterioration of the fluorescent member by detecting the intensity of the fluorescent light compared to the intensity of the excitation light.

19. The endoscope apparatus according to claim 18, wherein the control portion carries out control to stop emission of the excitation light from the light emitting device after detection of the deterioration of the fluorescent member.

20. An endoscope apparatus comprising:
an insertion section to be inserted into a space to be inspected;
a light emitting device for emitting excitation light;
a fluorescent member for emitting illumination light obtained by mixing the excitation light and fluorescent light excited by the excitation light into the space to be inspected from the tip end of the insertion section;
an optical sensor for detecting return light, which is a part of the illumination light;
a light guide for light detection provided with one end facing the fluorescent member and the other end facing the optical sensor for transmitting the return light emitted from the fluorescent member to the optical sensor;
a wavelength limiting member provided between the other end of the light guide for light detection and the optical sensor for limiting the wavelength of the return light; and
a light detection portion for detecting intensity of the return light detected at the optical sensor,
wherein the optical sensor comprises a first optical sensor for detecting the fluorescent light and a second optical sensor for detecting the excitation light.

21. The endoscope apparatus according to claim 20, wherein the light detection portion comprises a first light detection portion for detecting intensity of the florescent light detected at the first optical sensor and a second light detection portion for detecting intensity of the excitation light detected at the second optical sensor.

22. The endoscope apparatus according to claim 21, wherein the wavelength limiting member comprises a light splitter which transmits the excitation light out of the return light toward the second optical sensor and reflects the fluorescent light toward the first optical sensor or reflects the excitation light toward the second optical sensor and transmits the fluorescent light toward the first optical sensor.

23. The endoscope apparatus according to claim 22, further comprising
a control portion for controlling detection of deterioration of the fluorescent member from the intensity of the return light detected by the light detection portion,
wherein the control portion detects the intensity of the fluorescent light detected at the first optical sensor and detects the intensity of the excitation light detected at the second optical sensor; and
the control portion carries out control to detect deterioration of the fluorescent member by detecting the intensity of the fluorescent light compared to the intensity of the excitation light.

24. The endoscope apparatus according to claim 23, wherein the control portion carries out control to stop emission of the excitation light from the light emitting device after detection of the deterioration of the fluorescent member.

25. The endoscope apparatus according to claim 21, further comprising
a half mirror which splits the return light toward the first optical sensor and the second optical sensor,
wherein the wavelength limiting member comprises a first optical filter provided between the first optical sensor and the half mirror for transmitting only the fluorescent light out of the return light toward the first optical sensor and a second optical filter provided between the second optical sensor and the half mirror for transmitting only the excitation light out of the return light toward the second optical sensor.

26. The endoscope apparatus according to claim 25, further comprising
a control portion for controlling detection of deterioration of the fluorescent member from the intensity of the return light detected by the light detection portion,
wherein the control portion detects the intensity of the fluorescent light detected at the first optical sensor and detects the intensity of the excitation light detected at the second optical sensor; and
the control portion carries out control to detect deterioration of the fluorescent member by detecting the intensity of the fluorescent light compared to the intensity of the excitation light.

27. The endoscope apparatus according to claim 26, wherein the control portion carries out control to stop emission of the excitation light from the light emitting device after detection of the deterioration of the fluorescent member.

28. The endoscope apparatus according to claim 21, further comprising
a control portion for controlling output of the light emitting device based on a detection result of the first light detection portion and the second light detection portion.

29. The endoscope apparatus according to claim 20, further comprising
a control portion for controlling detection of deterioration of the fluorescent member from the intensity of the return light detected by the light detection portion,
wherein the wavelength limiting member transmits only the fluorescent light out of the return light and has only the fluorescent light detected by the optical sensor;
and the control portion detects the intensity of the fluorescent light detected at the optical sensor and carries out control to detect deterioration of the fluorescent member.

30. The endoscope apparatus comprising:
an insertion section to be inserted into a space to be inspected;
a light emitting device for emitting excitation light;
a fluorescent member for emitting illumination light obtained by mixing the excitation light and fluorescent light excited by the excitation light into the space to be inspected from the tip end of the insertion section;
an optical sensor for detecting return light, which is a part of the illumination light;
a light guide for light detection provided with one end facing the fluorescent member and the other end facing the optical sensor for transmitting the return light emitted from the fluorescent member to the optical sensor;
a wavelength limiting member provided between the other end of the light guide for light detection and the optical sensor for limiting the wavelength of the return light;
a light detection portion for detecting intensity of the return light detected at the optical sensor; and
a control portion for controlling output of the light emitting device based on a detection result of the light detection portion.

31. An endoscope apparatus comprising:
an insertion section to be inserted into a space to be inspected;
a light emitting device for emitting excitation light;
a fluorescent member for emitting illumination light obtained by mixing the excitation light and fluorescent light excited by the excitation light into the space to be inspected from the tip end of the insertion section;
an optical sensor for detecting return light, which is a part of the illumination light;
a light guide for light detection provided with one end facing the fluorescent member and the other end facing the optical sensor for transmitting the return light emitted from the fluorescent member to the optical sensor;
a wavelength limiting member provided between the other end of the light guide for light detection and the optical sensor for limiting the wavelength of the return light;
a light detection portion for detecting intensity of the return light detected at the optical sensor; and
a control portion for controlling detection of deterioration of the fluorescent member from the intensity of the return light detected by the light detection portion.

32. The endoscope apparatus according to claim 31, wherein the control portion carries out control to stop emission of the excitation light from the light emitting device after detection of the deterioration of the fluorescent member.

* * * * *

UNITED STATES PATENT AND TRADEMARK OFFICE
CERTIFICATE OF CORRECTION

PATENT NO.        : 7,455,638 B2                                                          Page 1 of 1
APPLICATION NO.   : 11/616694
DATED             : November 25, 2008
INVENTOR(S)       : Ogawa et al.

It is certified that error appears in the above-identified patent and that said Letters Patent is hereby corrected as shown below:

On the Title page, Item (30) Foreign Application Priority Data should read as follows:

Item (30)    Foreign Application Priority Data

Dec. 28, 2005   (JP) ...................................... 2005-380206

Signed and Sealed this

Seventeenth Day of March, 2009

JOHN DOLL
*Acting Director of the United States Patent and Trademark Office*